(12) United States Patent
Feleder et al.

(10) Patent No.: US 8,293,799 B2
(45) Date of Patent: Oct. 23, 2012

(54) OSMOTIC DEVICE CONTAINING A VENLAFAXINE SALT AND A SALT HAVING AN ION IN COMMON

(75) Inventors: Ethel C. Feleder, Buenos Aires (AR);
Glenn A. Meyer, Wilmington, NC (US);
Marcelo A. Ricci, Buenos Aires (AR);
Joaquina Faour, Buenos Aires (AR);
Ana C. Pastini, Buenos Aires (AR);
Marcelo F. Befumo, Buenos Aires (AR)

(73) Assignee: Osmotica Keresleedelmo és Szolgáltató KFT, Budapest (HU)

( * ) Notice: Subject to any disclaimer, the term of this patent is extended or adjusted under 35 U.S.C. 154(b) by 1524 days.

(21) Appl. No.: 11/010,829

(22) Filed: Dec. 13, 2004

(65) Prior Publication Data
US 2005/0163851 A1    Jul. 28, 2005

Related U.S. Application Data

(60) Provisional application No. 60/533,577, filed on Dec. 29, 2003.

(51) Int. Cl.
*A01N 33/02* (2006.01)
*A61K 31/135* (2006.01)
(52) U.S. Cl. .................... 514/648; 424/473
(58) Field of Classification Search .............. 514/648; 424/473
See application file for complete search history.

(56) References Cited

U.S. PATENT DOCUMENTS

| | | | |
|---|---|---|---|
| 4,801,461 A | 1/1989 | Hamel et al. | 424/467 |
| 5,458,887 A | 10/1995 | Chen et al. | 424/464 |
| 5,558,879 A | 9/1996 | Chen et al. | 424/480 |
| 5,654,005 A | 8/1997 | Chen et al. | 424/480 |
| 5,736,159 A | 4/1998 | Chen et al. | 424/480 |
| 5,785,994 A | 7/1998 | Wong et al. | 424/473 |
| 5,837,379 A | 11/1998 | Chen et al. | 424/465 |
| 5,866,164 A | 2/1999 | Kuczynski et al. | 424/472 |
| 6,004,582 A | 12/1999 | Faour et al. | 424/473 |
| 6,096,339 A * | 8/2000 | Ayer et al. | 424/473 |
| 6,294,201 B1 | 9/2001 | Kettelholt et al. | 424/473 |
| 6,352,721 B1 | 3/2002 | Faour | 424/473 |
| 6,387,403 B1 | 5/2002 | Seroff et al. | 424/473 |
| 6,491,949 B2 | 12/2002 | Faour et al. | 424/473 |
| 6,534,090 B2 | 3/2003 | Puthli et al. | 424/473 |
| 6,537,573 B2 | 3/2003 | Johnson et al. | 424/472 |
| 2001/0048943 A1 * | 12/2001 | Faour et al. | 424/465 |

(Continued)

OTHER PUBLICATIONS

Maj et al, The synergistic effect of amantadine and antidepressant drugs in the forced swimming test in rats, European Neuropsychopharmacology, vol. 10, Supplement 3, Sep. 2000, p. 255.*

(Continued)

*Primary Examiner* — Benjamin Packard
(74) *Attorney, Agent, or Firm* — Rick Matos; Innovar, L.L.C.

(57) ABSTRACT

The osmotic devices of the present invention include a single core comprising a salt of a drug and an osmotic salt, wherein the drug salt and the osmotic salt have a common ion. The release rate of the active drug is reduced, and the release profile of the active drug is modified, from a first order release profile to a zero order, pseudo-zero order, or sigmoidal release profile, by increasing the amount of the sodium chloride in the core of the device. In one embodiment the sodium chloride is used to modify a controlled release profile to a delayed and controlled release profile.

30 Claims, 3 Drawing Sheets

U.S. PATENT DOCUMENTS

2002/0099361 A1* 7/2002 Faour .................. 604/892.1

OTHER PUBLICATIONS

McClelland, G.A. et al., The Solubility-Modulated Osmotic Pump: In Vitro/In Vivo Release of Diltiazem Hydrochloride; Pharmaceutical Research, 1991, 8 (1), 88-92.

Ramakrishna, N. et al., Design and Evaluation of Osmotic Pump Tablets of Naproxen Sodium; Pharmazie, 2001, 56, 958-962.

Lin, Shan Yang et al., "Influence of Excipients, Drugs, and Osmotic Agent in the Inner Core . . . "; Journal of Pharm. Sci., 2002, 91 (9), 2040-2046.

Macheras, P., et al. "Modeling in Biopharmaceutics, Pharmacokinetics and Pharmacodynamics Homogeneous and Heterogeneous Approaches",2006, p. 82-83, Hardcover. ISBN: 978-0-387-28178-0.

* cited by examiner

OSMOTIC DEVICE CONTAINING A VENLAFAXINE SALT AND A SALT HAVING AN ION IN COMMON

CROSS-REFERENCE TO RELATED APPLICATIONS

This application claims priority to U.S. Provisional Patent Application Ser. No.: 60/533,577 entitled "Osmotic device containing a venlafaine salt and a salt having an ion in common" filed on Dec. 29, 2003, the entirety of which is hereby incorporated by reference.

FIELD OF THE INVENTION

This invention pertains to an osmotic device containing an active drug and an osmotic salt in the core, wherein the release rate of the active drug is reduced and the release profile of the active drug is modified by increasing the amount of the osmotic salt in the core. In one embodiment, the osmotic device contains venlafaxine hydrochloride and sodium chloride in the core. Depending upon the amount of sodium chloride present in the core, the osmotic device is capable of providing a sigmoidal, pseudo-zero order or zero order release of venlafaxine hydrochloride.

BACKGROUND OF THE INVENTION

Osmotic devices have demonstrated utility in delivering useful active agents such as medicines, nutrients, food products, pesticides, herbicides, germicides, algaecides, chemical reagents, and others known to those of ordinary skill to an environment of use in a controlled manner over prolonged periods of time. Known devices include tablets, pastilles, pills or capsules and others that use osmotic pressure to control the release of the active agent contained in the core of the osmotic device. Some osmotic devices may also include layers comprising one or more materials that are subject to erosion or that slowly dissolve in the environment of use thereby gradually dispensing the active agent.

Osmotic salts that exhibit an osmotic pressure gradient against an external fluid across the semipermeable wall of the osmotic devices have been used in the core of the osmotic devices for long time. U.S. Pat. No. 3,977,404, U.S. Pat. No. 4,008,719, U.S. Pat. No. 4,014,334, U.S. Pat. No. 4,034,758, and U.S. Pat. No. 4,077,407 to Theeuwes et al., U.S. Pat. No. 4,036,227 and U.S. Pat. No. 4,093,708 to Zaffaroni et al., describe that the osmotic salts are used mixed with an agent that has limited solubility in the external fluid with the osmotic salt forming a saturated solution containing agent that is osmotically delivered from the device. The osmotic salts are used by homogenously or heterogeneously mixing the osmotic salt or a mixture of them with an active agent, either before they are charged into the reservoir, or by self-mixing after they are charged into the reservoir. In operation, the osmotic salt attract fluid into the device producing a solution of the osmotic salt which is delivered from the device concomitantly transporting undissolved and dissolved agent to the exterior of the device. U.S. Pat. No. 6,248,359 and U.S. Pat. No. 6,599,532 to Faour, and U.S. Pat. No. 6,569,456, U.S. Pat. No. 6,572,890, U.S. Pat. No. 6,599,284, U.S. Pat. No. 6,599,532, U.S. Pat. No. 6,605,302, and U.S. Pat. No. 6,613,357 to Faour et al., and U.S. Pat. No. 6,521,255 to Vergez et al., teaches the osmotic salts will aid in either the suspension or dissolution of the active drug in the core. The osmotic salts can be incorporated to the core of the osmotic device to control the release of the active drug therefrom. All above referenced Patents do not disclose that the release rate of the active drug is reduced and the release profile of the active drug is modified by increasing the amount of the osmotic salt in the core.

The controlled release of active agents from an osmotic device can occur according to many different release profiles: first order, pseudo-first order, zero order, pseudo-zero order, sigmoidal, delayed, constant rate of release, pulsatile and some combinations thereof. Typically, a drug must have a solubility within the range of 50-300 mg/ml in order to be delivered effectively by an osmotic device.

It is generally well known that highly soluble drug salts can be difficult to formulate into osmotic devices. The more soluble they are, generally the more difficult they are to formulate into osmotic devices. This is because the drug salts tend to dissolve too quickly thereby leading to premature release of the drug, load dumping of the drug or rapid rather than controlled release of the drug. According to McClelland et al. (*Pharm. Res.* (1991), 8(1), 88-92), drugs with a water solubility of $\leq 50$ mg/ml should be released by an osmotic device in a controlled manner such that $\geq 95\%$ of the drug load is released according to zero-order kinetics. Drugs with a high water solubility (e.g., $\geq 300$ mg/ml) should be released by an osmotic device in a controlled manner such that only a very small percentage of the drug load is released according to zero-order kinetics. McClelland et al. therefore propose modulation of the drug solubility in an attempt to change the release profile of a drug from first order to zero order. In a particular embodiment, McClelland et al. demonstrate modulation of the solubility of diltiazem with sodium chloride in an osmotic device.

Due to the complexity of interactions occurring within the core of an osmotic device, no generally applicable approach has been developed to control and reduce the rate of dissolution of very water soluble drugs.

The use of sodium chloride as an osmagent in an osmotic device is widely known. The art generally teaches that increasing the amount of osmagent results in an increase of osmotic pressure and thereby an increase in the rate of release of drug from the core of the osmotic device. The prior art discloses osmotic devices having a bi-layered or multi-layered core, wherein at least one of the layers is a "push" or "displacement" layer comprising sodium chloride in combination with an osmopolymer or a water swellable polymer. The NaCl serves to draw water within the polymer matrix thereby wetting and swelling the polymer.

An osmotic device having a unitary core comprising a pharmaceutically acceptable salt of a drug in combination with sodium chloride and other excipients is known. In particular, the art discloses osmotic devices having a unitary core comprising drugs such as pseudoephedrine hydrochloride (Johnson et al. in U.S. Pat. No. 6,537,573; Faour et al. in U.S. Pat. No. 6,004,582; Hamel et al. in U.S. Pat. No. 4,801,461; Chen et al. in U.S. Pat. No. 5,458,887, U.S. Pat. No. 5,654,005, and U.S. Pat. No. 5,558,879), venlafaxine hydrochloride (Faour et al. in U.S. Pat. No. 6,352,721), reboxetine methane sulfonate (Seroff et al. in U.S. Pat. No. 6,387,403), carbamazepine (Puthli et al. in U.S. Pat. No. 6,534,090), rofecoxib (Faour et al. in U.S. Pat. No. 6,491,949), cisapride monohydrate (Faour et al. in U.S. Pat. No. 6,004,582), nifedipine (Kettelhoit et al. in U.S. Pat. No. 6,294,201); or other drugs (Chen et al. in U.S. Pat. No. 5,736,159 and U.S. Pat. No. 5,837,379) in combination with sodium chloride and other excipients. The art also discloses osmotic devices having bi-layered or multi-layered cores, wherein one of the layers includes a drug and sodium chloride among other excipients (Wong et al. in U.S. Pat. No. 5,785,994; Kuczynski et al. in U.S. Pat. No. 5,866,164). Osmotic devices having a bi-layered core comprising an active drug and sodium chloride in the drug-containing layer are disclosed in U.S. Pat. No. 6,352,721 to Faour, which teaches about three osmotic devices containing a core layer comprising venlafaxine hydrochloride and sodium chloride, cisapride and sodium chloride, and nifedipine and sodium chloride, respectively, U.S. Pat. No. 5,674,895, U.S. Pat. No. 5,840,754, U.S. Pat. No. 5,912,268, U.S. Pat. No. 6,124,355, U.S. Pat. No. 6,262,115 and U.S. patent application Ser. No. 20010005728, to Guittard et al., and U.S. patent application Ser. No. 20010009995 to Gupta et al., which disclose a core layer comprising oxybutynin and sodium chloride, and U.S. Pat. No. 6,387,403 to Seroff et al., which discloses a core layer comprising reboxetine methane sulfonate and sodium chloride. International documents WO03/039519 and WO03/039436 to Vergez et al., teach about osmotic devices comprising bi-layered cores comprising a drug in each layer of the core; drug-layer compositions comprising sodium chloride are exemplified, wherein the sodium chloride is among the osmagents that will aid in either the suspension or dissolution of the active drugs of the core. Osmotic devices having a multi-layered core are disclosed in U.S. Pat. No. 5,785,994 to Wong et al., wherein one of the layers includes a drug, such as diltiazem HCl, and potassium chloride among other excipients. In all above-referenced Patents, the osmotic salt is disclosed as an osmagent that increases the osmotic pressure of the core by attracting fluid into the device, and thereby producing a solution or suspension of the active drug that is then delivered from the device at increased rate. None of above-referenced Patents disclose that the release rate of the active drug is reduced and that the release profile of the active drug is modified by increasing the amount of the osmotic salt in the core. The weight percentages of sodium chloride and the drug as disclosed in the prior art are highly variable.

However, the art is not consistent regarding use of NaCl in osmotic devices. Ramakrishna et al. (*Pharmazie* (2001), 56(12), 958-962) disclose that increasing the amount of NaCl present in the core of an osmotic device is primarily responsible for decreasing the rate of release, delaying the initial release and affecting a zero order release of naproxen sodium.

McClelland et al. (1991) disclose that release of diltiazem hydrochloride from an osmotic device is slowed down by increasing the amount of NaCl added to the core of the osmotic device. They also report that the release profile can be changed from a first order release profile to a second order release profile. However, of particular interest, McClelland et al. specifically state that the NaCl must be present in controlled release form as NaCl crystals coated with cellulose acetate butyrate to form mini osmotic pumps. They state, "This pump-in-a-pump design was necessary to prevent the rapid depletion, and large attendant concentration variation, of the solubility modulating agent (sodium chloride) within the diltiazem hydrochloride core tablet environment." Accordingly, McClelland et al. teach that the desired effect provided by sodium chloride cannot be achieved with uncoated sodium chloride crystals.

The prior art also discloses the use of sodium chloride to reduce the rate of release or reduce the lag time in release of a drug salt from a coated controlled release device. Lin et al. (*J. Pharm. Sci.* (2002), 91(9), 2040-2046) disclose that increasing the amount of NaCl present in the core of a compression-coated ethylcellulose tablet reduces the lag time to initial drug release.

Accordingly, the art in this area is unpredictable, meaning that one cannot predict with certainty, or a priori, whether increasing the amount of sodium chloride in an osmotic pump containing a drug salt will decrease or increase the rate of release of the drug salt. This is particularly true for specific drug salt and osmotic salt combinations.

Venlafaxine, have been tested for the treatment of depression and symptoms of anxiety. EFFEXOR XR™ (venlafaxine hydrochloride) is commercially available in an extended release capsule dosage form from Wyeth Ayerst in 37.5, 75, and 150 mg strengths. The capsule is disclosed in U.S. Pat. No. 4,535,186. EFFEXOR XR™ is indicated for the treatment of depression and generalized anxiety disorder. Clinical depression is a disorder characterized by low self-esteem, guilt, self-reproach, introversion, sadness, despair, sleeping disorders, eating disorders or discouragement. Depression generally causes a lower or decrease of a person's function. Anxiety is a disorder characterized by responses to anticipation of unreal or imagined danger. It manifests itself as increased heart rate, altered respiration rate, sweating, trembling, weakness, or fatigue. Major depression and anxiety occur concomitantly in more patients than either one alone. When these disorders occur together, they are associated with more severe symptoms, increased impairment of function, a longer chronic course, poorer outcome, and a higher incidence of suicide.

U.S. Pat. No. 6,572,890 to Faour et al. discloses an osmotic device containing controlled release venlafaxine in the core in combination with an anti-psychotic agent in a rapid release external coat. The exemplified single core compositions contain venlafaxine but do not contain sodium chloride. The osmagents used in the core aid in either the suspension or dissolution of the VFX in the core, and can also be incorporated to the core of the osmotic device to control the release of VFX there from. Sodium chloride is not used to reduce the release rate and modify the release profile of the venlafaxine.

It is known in the field of osmotic devices that changing the release profile of a drug can have an effect upon the clinical benefit observed in a patient to which the osmotic device is administered. Depending upon the drug being administered, the disease or disorder being treated, the observed clinical response in a subject and other considerations, a particular controlled release profile will be preferred in providing an intended clinical benefit. In some situations, a zero order release profile is preferred while in others a first order release profile or a sigmoid release profile is observed.

Osmotic devices manufacture with two or more layers in order to provide a desired release rate profile can be difficult to produce and require specialized manufacturing machinery. Therefore, it would be an improvement in the art to provide a controlled release dosage form that is easily manufactured and produces a desired release rate or release rate profile for a desired soluble or insoluble hydrochloride salt of an active agent by modifying the amount of sodium chloride in the core of the osmotic device.

SUMMARY OF THE INVENTION

The invention provides a method of reducing the rate of release of drug salt from the core of an osmotic device. The drug, which is an organic base, is present as a pharmaceutically acceptable salt, such as formed by an amine-containing drug forming a salt complex with a mineral acid. In particular embodiments, the drug is a hydrochloride salt. In one embodiment, the drug is a salt of venlafaxine, esp. venlafaxine hydrochloride, and the osmotic salt is an alkali metal salt of a mineral acid, esp. sodium chloride or potassium chloride. The drug salt is generally a mineral acid salt of the drug.

The method requires the step of including in a drug-containing core an amount of osmotic salt, esp. sodium chloride, that is sufficient to reduce the rate of release of the drug salt and modify the release profile of the active drug. The drug salt is present in an amount sufficient to provide a sigmoidal, pseudo-zero order or zero order release of drug salt. For example, a first amount of sodium chloride provides a first release rate and a second greater amount of sodium chloride provides a slower release rate in two similar osmotic devices.

The invention also includes an osmotic device with a core comprising a drug salt, an osmotic salt, and at least one other pharmaceutical excipient, wherein the drug salt and osmotic salt have a common ion. The osmotic salt is present in an amount sufficient to slow the rate of release of drug as compared to the rate of release of drug from an otherwise same dosage form containing a lower amount of or excluding osmotic salt. This behavior will occur only after the amount of sodium chloride present has exceeded a particular molar ratio with respect to the drug. The osmotic salt can also delay the initial release of the drug as compared to an otherwise similar osmotic device containing a lower amount of osmotic salt.

The present osmotic device overcomes many of the disadvantages inherent in related prior art osmotic devices because it is capable of providing sigmoidal, pseudo-zero order or zero order release of a very water soluble drug salt from an osmotic device. The dosage form of the invention optionally includes a delayed release of drug salt, wherein the delay in release is due to the amount of NaCl present in the dosage form.

Specific embodiments of the invention include those embodiments wherein: a) the drug is venlafaxine hydrochloride or an analogue or derivative; b) the drug is released from the osmotic device according to a zero order, pseudo zero order or sigmoidal controlled release profile after exposure to an environment of use; c) the drug is released according to a zero order or pseudo-zero order controlled release profile for a predetermined period of hours after exposure to an environment of use; d) initial release of the drug is delayed for a predetermined period of hours after exposure of the device to an environment of use; e) the osmotic salt present in the dosage form is not coated with a material that delays or slows its dissolution in an environment of use; f) the osmotic salt is sodium chloride; g) the oral administration of the venlafaxine-containing osmotic device results in lower incidence of treatment-emergent adverse effects typically associated with the administration of venlafaxine with other osmotic devices; h) the venlafaxine osmotic device further comprises a second active drug in the core; 24) the second active drug in the core is an NMDA receptor antagonist selected from the group consisting of amantadine, memantine and ifenprodil; and I) the second active drug in the core is amantadine.

One aspect of the invention provides an osmotic device comprising:
  a unitary core comprising venlafaxine salt, one or more excipients and osmotic salt wherein the weight ratio of venlafaxine salt to osmotic salt ranges from 0.35:1 to 150:1; and
  a membrane surrounding the core and having one or more passageways there through;
  wherein the drug salt is released through the one or more passageways according to a zero-order, pseudo-zero, or sigmoidal controlled release profile, optionally wherein release of venlafaxine salt is delayed for a period of time, when the osmotic device is exposed to an aqueous environment of use, and wherein the drug salt and osmotic salt have a common ion.

Another aspect of the invention provides an osmotic device comprising:
  a unitary core comprising a mixture of a hydrochloride salt of a drug, one or more excipients and sodium chloride, wherein crystals of the sodium chloride are not coated with cellulose acetate butyrate; and
  a membrane surrounding the core and having one or more passageways there through;
  wherein the drug salt is released through the one or more passageways according to a zero-order, pseudo-zero, or sigmoidal controlled release profile, optionally wherein release of venlafaxine salt is delayed for a period of time, when the osmotic device is exposed to an aqueous environment of use, and wherein the drug is not pseudoephedrine or oxybutynin.

Still another aspect of the invention provides an osmotic device comprising:
  a unitary core comprising venlafaxine hydrochloride, one or more excipients, and sodium chloride; and
  a membrane surrounding the core and having one or more passageways there through, the membrane having a controlled porosity or permeability adapted to cooperate with the sodium chloride to provide a predetermined release profile for venlafaxine hydrochloride;
  wherein the sodium chloride is present in an amount sufficient such that venlafaxine hydrochloride is released through the one or more passageways according to a zero-order, pseudo-zero, or sigmoidal controlled release profile, optionally wherein release of venlafaxine salt is delayed for a period of time, when the osmotic device is exposed to an aqueous environment of use.

The osmotic device can also be employed in a method of treating or preventing a disorder, disease or symptom responsive to venlafaxine therapy, the method comprising the step of:
  administering to a subject an osmotic device according to any one of claims 1-7, wherein the side effects observed in the subject are of lesser occurrence or severity than the side effects observed in the same subject administered another osmotic device comprising substantially the same amount of venlafaxine hydrochloride but releasing the venlafaxine hydrochloride according to a different release profile.

Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
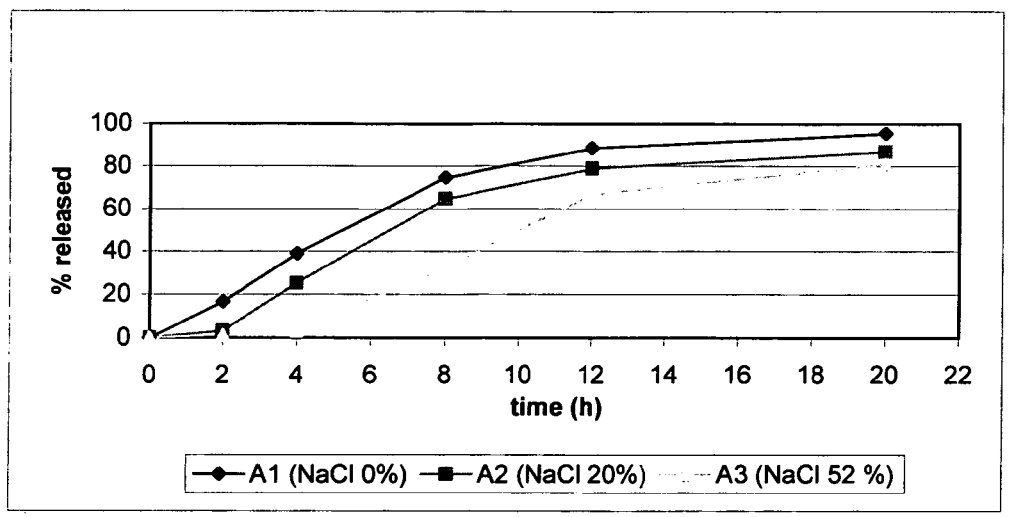
FIG. 1 depicts an in vitro release profile of venlafaxine hydrochloride from an exemplary osmotic device comprising coating A made according to Example 1

The invention may be better understood by reference to the following definitions provided herein.

By "immediate release" is meant a release of an active agent to an environment over a period of seconds to no more than about 30 minutes once release has begun and release begins within a second to no more than about 15 minutes after administration.

By "rapid release" is meant a release of an active agent to an environment over a period of 1-59 minutes or 1 minute to three hours once release has begun and release can begin within a few minutes after administration or after expiration of a delay period (lag time) after administration.

By "controlled release" is meant a release of an active agent to an environment over a period of about eight hours up to about 12 hours, 16 hours, 18 hours, 20 hours, a day, or more than a day. A controlled release device can be a sustained release or extended release device. By "sustained release" is meant a controlled release of an active agent to maintain a constant drug level in the blood or target tissue of a subject to which the device is administered. By "extended release" is meant a controlled release of an active agent from a dosage form to an environment over an extended period of time. A controlled release device generally effects at least a two-fold reduction in dosing frequency as compared to the drug presented in a conventional dosage form (e.g., a solution or rapid releasing conventional solid dosage forms).

A delayed but controlled release dosage form is one that provides a delayed release of a drug followed by a controlled release of the drug. By delayed release is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, or 30 minutes to 10 hours, or 1 hour to 10 hours.

A zero-order release profile characterizes the release profile of a dosage form that releases a constant amount of drug per unit time. A pseudo-zero order release profile is one that approximates a zero-order release profile.

A first order release profile characterizes the release profile of a dosage form that releases a constant percentage of an initial drug charge per unit time. A pseudo-first order release profile is one that approximates a first order release profile.

By "unitary core" is meant the core of an osmotic device that is not divided into two or more layers or laminas. The core is considered to be the composition enclosed within the semipermeable membrane of the osmotic device.

Venlafaxine hydrochloride is available commercially from companies such as Uquifa Mexico S. A. de C. V. (Morelos, Mexico), Teva Group (Beer Sheva), and Alembic Ltd (Gujarat, India).

The invention provides for the administration of venlafaxine in its free base, free acid, racemic, optically pure, diastereomeric and/or pharmaceutically acceptable salt forms.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral and organic acid salts of the VFX. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the organic salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, benzenesulfonic, ethane disulfonic, oxalic, isethionic, and other acids known to those of ordinary skill in the art. Lists of suitable salts are found in *Remington's Pharmaceutical Sciences,* 17th ed., Mack Publishing Company, Easton, Pa., 1985, p. 1418, the disclosure of which is hereby incorporated by reference.

The release profiles of the osmotic device tablets of the invention will vary according to the amount of osmotic salt, esp. sodium chloride, present in the core.

FIG. 1 depicts venlafaxine hydrochloride in vitro dissolution profiles for the osmotic device tablets described in Example 1. The in vitro testing was performed with USP Type II dissolution apparatus (paddles) in 800 ml of distilled water with a fixed agitation rate of 50 revolutions per minute, maintained at a temperature of 37±0.5° C. The samples were tested by high pressure liquid chromatography.

The release profiles obtained for six tablets (#1-#6) of the formulation containing 0% of sodium chloride and coating A (FIG. 1, $A_1$) are disclosed in the table below, which detail the amount of venlafaxine released at the indicated time points, based upon when the osmotic device was exposed to the release liquid medium.

| Time  | Released % | | | | | | Mean | SD | Range (%) | |
|---|---|---|---|---|---|---|---|---|---|---|
| (hrs) | #1 | #2 | #3 | #4 | #5 | #6 | (%) | (%) | Max | Min |
| 2  | 17.7 | 15.5 | 17.3 | 13.8 | 16.3 | 18.8 | 16.6 | 1.8 | 18.8 | 13.8 |
| 4  | 38.6 | 38.7 | 39.6 | 34.4 | 39.9 | 41.5 | 38.8 | 2.4 | 41.5 | 34.4 |
| 8  | 74.9 | 76.3 | 75.3 | 70.9 | 75.1 | 76.3 | 74.8 | 2.0 | 76.3 | 70.9 |
| 12 | 87.8 | 89.4 | 89.8 | 86.9 | 88.7 | 88.7 | 88.5 | 1.1 | 89.8 | 86.9 |
| 20 | 96.2 | 94.7 | 98.1 | 94.6 | 94.8 | 93.8 | 95.4 | 1.6 | 98.1 | 93.8 |

The release profiles obtained for six tablets (#1-#6) of the formulation containing 20% of sodium chloride and coating A (FIG. 1, $A_2$) are disclosed in the table below, which detail the amount of venlafaxine released at the indicated time points, based upon when the osmotic device was exposed to the release liquid medium.

| Time  | Released % | | | | | | Mean | SD  | Range (%) | |
|-------|------|------|------|------|------|------|------|------|------|------|
| (hrs) | #1   | #2   | #3   | #4   | #5   | #6   | (%)  | (%)  | Max  | Min  |
| 2     | 2.1  | 2.3  | 4.3  | 4.4  | 2.7  | 3.8  | 3.3  | 1.0  | 4.4  | 2.1  |
| 4     | 25.7 | 22.8 | 26.4 | 28.6 | 23.6 | 24.2 | 25.2 | 2.1  | 28.6 | 22.8 |
| 8     | 66.3 | 62.9 | 65.7 | 67.9 | 62.8 | 63.6 | 64.9 | 2.1  | 67.9 | 62.8 |
| 12    | 80.2 | 78   | 79.3 | 81.5 | 77.4 | 78.4 | 79.1 | 1.5  | 81.5 | 77.4 |
| 20    | 87.5 | 85.9 | 86.8 | 88.6 | 86.1 | 86.7 | 86.9 | 1.0  | 88.6 | 85.9 |

The release profiles obtained for six tablets (#1-#6) of the formulation containing 52% of sodium chloride and coating A (FIG. 1, $A_3$) are disclosed in the table below, which detail the amount of venlafaxine released at the indicated time points, based upon when the osmotic device was exposed to the release liquid medium.

| Time  | Released % | | | | | | Mean | SD  | Range (%) | |
|-------|------|------|------|------|------|------|------|------|------|------|
| (hrs) | #1   | #2   | #3   | #4   | #5   | #6   | (%)  | (%)  | Max  | Min  |
| 2     | 1.5  | 1.4  | 1.1  | 1.4  | 1.7  | 1.3  | 1.4  | 0.2  | 1.7  | 1.1  |
| 4     | 3.7  | 3.2  | 2.1  | 3.1  | 3.7  | 2.7  | 3.1  | 0.6  | 3.7  | 2.1  |
| 8     | 38.0 | 44.4 | 5.7  | 24.9 | 50.8 | 29.2 | 32.2 | 16.1 | 50.8 | 5.7  |
| 12    | 67.1 | 73.5 | 55.5 | 63.5 | 72.8 | 68.8 | 66.9 | 6.7  | 73.5 | 55.5 |
| 20    | 78.5 | 84.1 | 76.3 | 79.9 | 85.0 | 84.1 | 81.3 | 3.6  | 85   | 76.3 |

The release profiles obtained for six tablets (#1-#6) of the formulation containing 0% of sodium chloride and coating B (FIG. 2, $B_1$) are disclosed in the table below, which detail the amount of venlafaxine released at the indicated time points, based upon when the osmotic device was exposed to the release liquid medium.

| Time  | Released % | | | | | | Mean | SD  | Range (%) | |
|-------|------|------|------|------|------|------|------|------|------|------|
| (hrs) | #1   | #2   | #3   | #4   | #5   | #6   | (%)  | (%)  | Max  | Min  |
| 1     | 4.6  | 4    | 4.6  | 6    | 7.3  | 5.9  | 5.4  | 1.2  | 7.3  | 4.0  |
| 2     | 12.7 | 13.6 | 15   | 15.2 | 17.4 | 16   | 15.0 | 1.7  | 17.4 | 12.7 |
| 4     | 27.2 | 30.3 | 31.3 | 31.2 | 34.5 | 33   | 31.2 | 2.5  | 34.5 | 27.2 |
| 8     | 50.4 | 54.6 | 55.5 | 54.6 | 58.3 | 57   | 55.1 | 2.7  | 58.3 | 50.4 |
| 12    | 65.7 | 70.7 | 72.2 | 70.3 | 73.8 | 73   | 70.9 | 2.9  | 73.8 | 65.7 |
| 20    | 78.4 | 84.8 | 86.8 | 84.5 | 87.8 | 87   | 84.9 | 3.5  | 87.8 | 78.4 |

The release profiles obtained for six tablets (#1-#6) of the formulation containing 5% of sodium chloride and coating B (FIG. 2, $B_2$) are disclosed in the table below, which detail the amount of venlafaxine released at the indicated time points, based upon when the osmotic device was exposed to the release liquid medium.

| Time  | Released % | | | | | | Mean | SD  | Range (%) | |
|-------|------|-------|------|-------|------|------|------|------|-------|------|
| (hrs) | #1   | #2    | #3   | #4    | #5   | #6   | (%)  | (%)  | Max   | Min  |
| 1     | 3.8  | 5.0   | 3.5  | 2.4   | 1.1  | 2.9  | 3.1  | 1.3  | 5.0   | 1.1  |
| 2     | 16.3 | 19.9  | 16.6 | 16.3  | 13.3 | 15.8 | 16.4 | 2.1  | 19.9  | 13.3 |
| 4     | 38.1 | 42.9  | 38.9 | 39.2  | 35.1 | 38.2 | 38.7 | 2.5  | 42.9  | 35.1 |
| 8     | 68.5 | 73.3  | 71.1 | 71.9  | 64.4 | 67.8 | 69.5 | 3.3  | 73.3  | 64.4 |
| 12    | 84.7 | 90.0  | 88.3 | 89.4  | 82.3 | 84.5 | 86.5 | 3.1  | 90.0  | 82.3 |
| 20    | 96.0 | 100.0 | 97.9 | 100.2 | 94.7 | 95.9 | 97.5 | 2.3  | 100.2 | 94.7 |

The release profiles obtained for six tablets (#1-#6) of the formulation containing 10% of sodium chloride and coating B (FIG. 2, $B_3$) are disclosed in the table below, which detail the amount of venlafaxine released at the indicated time points, based upon when the osmotic device was exposed to the release liquid medium.

| Time  | Released % |      |      |       |      |      | Mean | SD   | Range (%) |      |
|-------|------|------|------|-------|------|------|------|------|-------|------|
| (hrs) | #1   | #2   | #3   | #4    | #5   | #6   | (%)  | (%)  | Max   | Min  |
| 1     | 0.3  | 0.6  | 0.6  | 0.3   | 0.7  | 0.4  | 0.5  | 0.1  | 0.7   | 0.3  |
| 2     | 2.2  | 5.2  | 4.1  | 4.5   | 3.2  | 4.9  | 4.0  | 1.1  | 5.2   | 2.2  |
| 4     | 21.0 | 26.1 | 25.6 | 27.4  | 23.2 | 27.4 | 25.1 | 2.5  | 27.4  | 21.0 |
| 8     | 61.2 | 65.3 | 64.9 | 69.2  | 62.0 | 66.2 | 64.8 | 2.9  | 69.2  | 61.2 |
| 12    | 84.3 | 86.2 | 86.6 | 91.4  | 83.1 | 86.8 | 86.4 | 2.8  | 91.4  | 83.1 |
| 20    | 94.7 | 96.6 | 98.8 | 102.1 | 96.2 | 99.2 | 97.9 | 2.7  | 102.1 | 94.7 |

The release profiles obtained for six tablets (#1-#6) of the formulation containing 20% of sodium chloride and coating B (FIG. 2, $B_4$) are disclosed in the table below, which detail the amount of venlafaxine released at the indicated time points, based upon when the osmotic device was exposed to the release liquid medium.

| Time  | Released % |      |      |       |      |      | Mean | SD   | Range (%) |      |
|-------|------|------|------|-------|------|------|------|------|-------|------|
| (hrs) | #1   | #2   | #3   | #4    | #5   | #6   | (%)  | (%)  | Max   | Min  |
| 1     | 0.1  | 0.3  | 0.5  | 0.2   | 0.4  | 0.5  | 0.3  | 0.2  | 0.5   | 0.1  |
| 2     | 2.1  | 5.0  | 4.4  | 4.2   | 4.3  | 5.3  | 4.2  | 1.1  | 5.3   | 2.1  |
| 4     | 18.9 | 26.0 | 26.0 | 25.5  | 25.1 | 26.5 | 24.7 | 2.9  | 26.5  | 18.9 |
| 8     | 56.0 | 62.9 | 62.6 | 65.2  | 60.8 | 64.5 | 62.0 | 3.3  | 65.2  | 56.0 |
| 12    | 79.7 | 85.3 | 83.2 | 88.0  | 81.5 | 85.3 | 83.8 | 3.0  | 88.0  | 79.7 |
| 20    | 96.5 | 99.4 | 97.1 | 100.3 | 93.6 | 97.5 | 97.4 | 2.4  | 100.3 | 93.6 |

The release profiles obtained for six tablets (#1-#6) of the formulation containing 30% of sodium chloride and coating B (FIG. 2, $B_5$) are disclosed in the table below, which detail the amount of venlafaxine released at the indicated time points, based upon when the osmotic device was exposed to the release liquid medium.

| Time  | Released % |      |      |      |      |      | Mean | SD   | Range (%) |      |
|-------|------|------|------|------|------|------|------|------|------|------|
| (hrs) | #1   | #2   | #3   | #4   | #5   | #6   | (%)  | (%)  | Max  | Min  |
| 1     | 0.3  | 0.1  | 0.2  | 0.2  | 0.1  | 0.1  | 0.2  | 0.1  | 0.3  | 0.1  |
| 2     | 0.9  | 0.3  | 0.7  | 1.0  | 0.5  | 0.3  | 0.6  | 0.3  | 1.0  | 0.3  |
| 4     | 3.2  | 1.1  | 3.7  | 4.0  | 2.9  | 0.9  | 2.6  | 1.3  | 4.0  | 0.9  |
| 8     | 22.6 | 18.9 | 29.7 | 28.2 | 28.3 | 19.8 | 24.6 | 4.8  | 29.7 | 18.9 |
| 12    | 53.0 | 53.8 | 63.6 | 57.9 | 62.9 | 56.8 | 58.0 | 4.5  | 63.6 | 53.0 |
| 20    | 79.8 | 79.8 | 81.2 | 79.5 | 83.7 | 80.7 | 80.8 | 1.6  | 83.7 | 79.5 |

Figure 2:
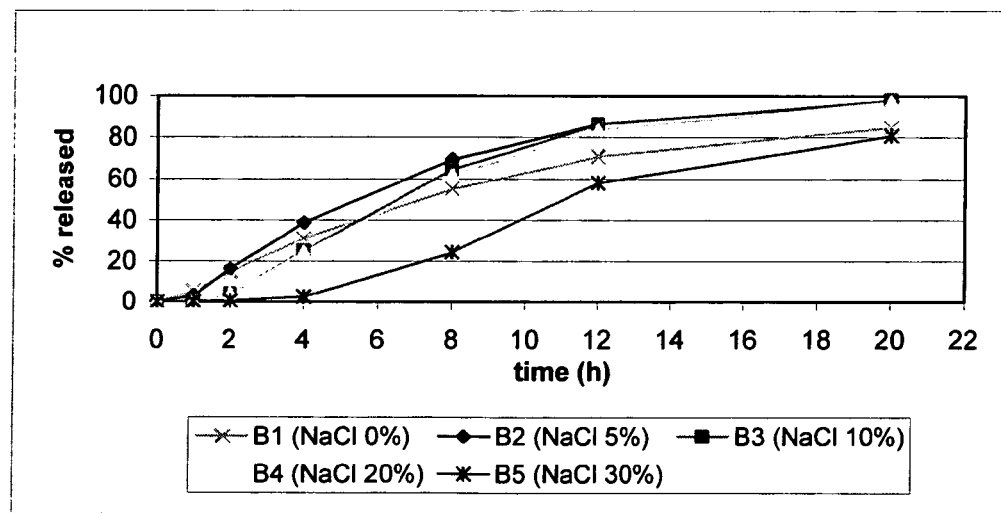
FIG. 2 depicts an in vitro release profile of venlafaxine hydrochloride from an exemplary osmotic device comprising coating B made according to Example 1.

The increase of the amount of sodium chloride in the core coated with coating formulations A and B of the venlafaxine osmotic device tablets of Example 1, reduces the rate of release of venlafaxine, and modifies the release profile of venlafaxine from a first order release profile to a sigmoid release profile as shown in FIGS. 1 and 2 respectively.

The values set forth in the above tables are approximate numbers. Depending upon the conditions of measurement as well as the assay used to determine those values, they may have a standard deviation of ±5% or ±10% of the indicated value.

The osmotic device of the invention can comprise a water soluble and/or erodible coating, inert or drug-containing. The water soluble and/or erodible coating, inert or drug-containing will generally comprise an inert and non-toxic material which is at least partially, and optionally substantially completely, soluble or erodible in an environment of use. Selection of materials suitable for the inert or drug-containing water soluble coatings will depend upon the desired release rate of drug from the drug-containing coating and upon the desired separation of drug delivery from the core versus the drug-containing coating. A rapidly dissolving coat will be soluble in the buccal cavity and/or upper GI tract, such as the stomach, duodenum, jejunum or upper small intestines. Exemplary materials are disclosed in U.S. Pat. No. 4,576,604 to Guittard et al. and U.S. Pat. No. 4,673,405 to Guittard et al., and U.S. Pat. No. 6,004,582 to Faour et al. and the text *Pharmaceutical Dosage Forms: Tablets Volume I, $2^{nd}$ Edition.* (A. Lieberman. ed. 1989, Marcel Dekker, Inc.), the relevant disclosures of which are hereby incorporated by reference. In some embodiments, the rapidly dissolving coat will be soluble in saliva, gastric juices, or acidic fluids.

Materials which are suitable for making the water soluble and/or erodible coatings of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film-forming polymers.

Other materials which can be used in the water soluble and/or erodible coatings include hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the water soluble coat.

The inert water soluble and/or erodible coat covering the semipermeable wall and blocking the passageway is made of synthetic or natural material which, through selective dissolution or erosion allows the passageway to become unblocked thus allowing the process of osmotic delivery to start. This slow or fast dissolving water soluble coat can be impermeable to a first external fluid, while being soluble in a second external fluid. This property can help to achieve a controlled and selective release of the active compound in the nucleus.

In some embodiments, the inert water soluble and/or erodible coat will be insoluble in the fluid of a first environment of use, such as gastric juices, acidic fluids, or polar liquids, and soluble or erodible in the fluid of a second environment of use, such as intestinal juices, substantially pH neutral or basic fluids, or a polar liquids. A wide variety of other polymeric materials are known to possess these various solubility properties and can be included in the water soluble coat. Such other polymeric materials include, by way of example and without limitation, cellulose acetate phthalate (CAP), cellulose acetate trimelletate (CAT), poly(vinyl acetate)phthalate (PVAP), hydroxypropyl methylcellulose phthalate (HP), poly (methacrylate ethylacrylate) (1:1) copolymer (MA-EA), poly (methacrylate methylmethacrylate) (1:1) copolymer (MA-MMA), poly(methacrylate methylmethacrylate) (1:2) copolymer, Eudragit™ L-30-D (MA-EA, 1:1), Eudragit™ L-100-55 (MA-EA, 1:1), hydroxypropylmethylcellulose acetate succinate (HPMCAS), Coateric™ (PVAP), Aquateric™ (CAP), AQOA™ (HPMCAS) and combinations thereof. The water soluble coat can also comprise dissolution aids, stability modifiers, and bioabsorption enhancers.

An optional polymeric material for use in the inert water soluble and/or erodible coat includes enteric materials that resist the action of gastric fluid avoiding permeation through the semipermeable wall while one or more of the materials in the core are solubilized in the intestinal tract thereby allowing delivery of a drug in the core by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The water soluble and/or erodible coat can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon™ K 30 has a viscosity of about 5.5-8.5 cps at 20.degree. C., and a 2% P/V aqueous solution of Methocel™ E-15 has a viscosity of about 13-18 cps at 20.degree. C.

The inert water soluble and/or erodible coat can also comprise other materials suitable which are substantially resistant to gastric juices and which will promote either enteric or colonic release. For this purpose, the inert water soluble and/or erodible coat can comprise one or more materials that do not dissolve, disintegrate, or change their structure in the stomach and during the period of time that the osmotic device resides in the stomach. Representative materials that keep their integrity in the stomach can comprise a member selected from the group consisting of (a) keratin, keratin sandaractolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized crosslinked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethylmethacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials that form a semipermeable wall which are known by those of ordinary skill in the art of pharmaceutical sciences are suitable for this purpose. Exemplary materials are cellulose esters, cellulose ethers and cellulose esters-ethers. However, it has been found that a semipermeable membrane comprising cellulose acetate (CA) and poly(ethylene glycol) (PEG), in particular PEG 400, performs well when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50-99% by weight of CA:about 50-1% by weight of PEG, and about 95% by weight of CA:about 5% by weight of PEG. The ratio can be varied to alter permeability and ultimately the release profile of the osmotic device. Other suitable materials can include a selected member of the group of cellulose acylates such as cellulose acetate, cellulose diacetate, cellulose triacetate and combinations thereof. Many suitable polymers, include those disclosed in Argentine Patent No. 199,301, U.S. Pat. No. 6,004,582 and references cited herein, the disclosures of which are hereby incorporated by reference.

Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%; a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. No. 3,173,876, U.S. Pat. No. 3,276,586, U.S. Pat. No. 3,541,005, U.S. Pat. No. 3,541,006, and U.S. Pat. No. 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride), semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. These and others polymers are disclosed in U.S. Pat. No. 3,845,770, U.S. Pat. No. 3,916,899, U.S. Pat. No. 4,765,989 and U.S. Pat. No. 4,160,020; and in *Handbook of Common Polymers* (Scott, J. R. and Roff, W. J., eds.; 1971; CRC Press, Cleveland, Ohio).

Plasticizers can be included in the present device to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) *Chemistry: Biotechnical and Biomedical Applications* (J. M. Harris, Ed.; Plenum Press, NY) the disclosure of which is hereby incorporated by reference.

An alternative embodiment of the invention includes pore former(s) in the wall to form additional passageways over time.

Release of active agent from the core can be delayed such that the release profile of active agent will exhibit delayed and then controlled release. Such a device would be termed a delayed controlled release device.

The osmotic device of the invention comprises at least one passageway (pore, hole, or aperture) that communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

The preformed passageway in the wall is typically generated by mechanical means, such as perforation by a laser or drill, or any other similar method known to those of ordinary skill in the art. The passageway is generally formed by controlled laser perforation, using an apparatus similar to that disclosed in Theeuwes et al. '864, the entire disclosure of which is incorporated herein by reference. Specific embodiments of the controlled laser perforation method will vary according to the equipment used. The laser equipment of Theeuwes et al. '864 can be modified as described herein to prepare an osmotic device according to the invention. Other suitable laser equipment, are methods of use thereof, are disclosed in Emerton et al. '793 and Roy '771, the entire disclosures of which are hereby incorporated by reference. The process and system of Faour (U.S. Pregrant Patent Publication No. 2002/0099361) can also be used to form the preformed passageway and/or etch in the wall.

A preformed passageway can be made to substantially retain its size during use of the device or it can be made to increase in size during use of the dosage form. Preformed passageways of different sizes, shapes and functions can be used.

The preformed passageway in the wall may dissolve or tear in a predetermined or random manner, and the shape of the preformed passageway after enlargement can be made to approximate a predetermined or randomly determined shape. The extent to which a passageway increases in size can also be related to the viscosity, molecular weight or degree of substitution of the at least one excipient. Generally, increasing the viscosity, molecular weight, or degree of substitution of the at least one excipient will increase the extent to which the passageway increases in size.

A device according to the present invention can comprise one or more preformed passageways including two, three, four, five, six, seven, eight, nine, ten or more preformed passageways. It is only necessary that the preformed passageways together are adapted to permit controlled release of ingredients from the core during use.

The core of the osmotic device of the present invention will comprise an active agent and an osmotic agent and can further comprise many other materials as discussed herein. The amount of active agent present can vary as described above for the external coat. Generally, the active agent will be present in an amount ranging from 0.1-99.9% by weight of the uncoated core. Specific ranges will vary according to the active agent used and the intended use of the osmotic device.

When the active agent is of limited solubility in the environment of use, osmotically effective solutes or osmotic agents, i.e. osmagents, that are capable of being totally or partially solubilized in the fluid, are added. These osmagents will aid in either the suspension or dissolution of the active agent in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, magnesium succinate, sodium succinate, sodium butyrate, sodium fumarate, sodium benzenesulfonate, sodium toluenesulfonate, sodium methanesulfonate, combinations thereof and other similar or equivalent materials which are widely known in the art. U.S. Pat. No. 4,077,407 to Theeuwes et al., the entire disclosure of which is hereby incorporated by reference, discloses suitable osmagents.

These osmagents can also be incorporated to the core of the osmotic device to control the release of an active agent therein. When the agent is (components of the care are) only partially or incompletely soluble in the fluid of an environment of use, it can be released as a suspension provided sufficient fluid has been imbibed or absorbed by the core to form a suspension. When the active agent is (components of the core are) soluble in the fluid, the active agent is released as a liquid.

One or more osmopolymers can also be added to the core of the device to aid in the delivery of active agents. Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyl-lactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides. These materials swell or expand to an equilibrium state when exposed to water or other biological fluids. This volume expansion is used to physically force the pharmaceutical agent out through openings that have been formed in the wall, shell or coating during manufacture. A water insoluble active agent is primarily released as insoluble particles, which therefore have limited bioavailability. Exemplary osmopolymers are disclosed in U.S. Pat. No. 5,422,123; U.S. Pat. No. 4,783,337; U.S. Pat. No. 4,765,989; U.S. Pat. No. 4,612,008; U.S. Pat. No. 4,327,725; U.S. Pat. No. 4,609,374; U.S. Pat. No. 4,036,228; U.S. Pat. No. 4,992,278; U.S. Pat. No. 4,160,020; U.S. Pat. No. 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in one embodiment, lightly cross-linked, such as cross-links being formed by covalent or ionic bonds.

The osmotic device of the invention can also comprise an adsorbent, antioxidant, buffering agent, colorant, flavorant, sweetening agent, antiadherent, binder, diluent, direct compression excipient, disintegrant, glidant, lubricant, opaquant and/or polishing agent.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean a substance used to cause adhesion of powder particles in tablet granulations. Such compounds include, by way of example and without limitation, acacia, alginic acid, carboxymethylcellulose sodium, poly(vinylpyrrolidone), compressible sugar (e.g., NuTab™), ethylcellulose, gelatin, liquid glucose, methylcellulose, povidone and pregelatinized starch and other materials known to one of ordinary skill in the art.

When needed, a binder may also be included in the present device. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and others known to those of ordinary skill. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "diluent" or "filler" is intended to mean an inert substance used as filler to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "polishing agent" is intended to mean a compound used to impart an attractive sheen to coated tablets. Such compounds include, by way of example and without limitation, carnauba wax, and white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present device can also employ one or more commonly known surface active agents or cosolvents that improve wetting or disintegration of the osmotic device core or layers.

It is contemplated that the osmotic device of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly (oxypropylene) copolymers; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, I-poly(lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of therapeutic compound incorporated in each device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient.

The term "unit dosage form" is used herein to mean a device containing a quantity of the therapeutic compound, said quantity being such that one or more predetermined units may be provided as a single therapeutic administration.

The device of the invention can be prepared according to the methods disclosed herein or those well known in the art. For example, according to one manufacturing technique, the active agent and excipients that comprise the core can be mixed in solid, semisolid or gelatinous form, then moistened and sieved through a specified screen to obtain a granulate. The granulate is then dried in a dryer and compressed, for example, by punching to form uncoated cores. The compressed and uncoated cores are then covered with a solution of suitable materials that comprise the wall. Subsequently, the wall surrounding each core is perforated with, for example, laser equipment to form the preformed passageway in the manner previously described. If desired, the device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The dosage form of the invention is used in various methods of treating diseases, disorders and/or symptoms that are responsive to venlafaxine therapy. By "responsive to venlafaxine therapy" is meant that the frequency of occurrence or severity of the undesired symptom, disorder or disease will be reduced in a subject after administration of one or more dosage forms of the invention for a sufficient period of time, e.g., one day, 2-4 days, a week, 2-3 weeks, a month, 2-6 months or more, to obtain the desired result.

Symptoms, disorders and/or diseases that are responsive to venlafaxine therapy include, but are not limited to, affective disorders such as depression, bipolar and manic disorders, attention deficit disorder, attention deficit disorder with hyperactivity, Parkinson's disease, Alzheimer's disease, epilepsy, cerebral function disorders, obesity and weight gain, incontinence, dementia, fibromyalgia, agoraphobia, obsessive compulsory disorder, social anxiety disorder, autism, schizophrenia, obesity, anorexia nervosa, bulimia nervosa, Gilles de la Tourette Syndrome, vasomotor flushing, cocaine and alcohol addiction, sexual dysfunction, borderline personality disorder, chronic fatigue syndrome, urinary incontinence, pain, Shy Drager syndrome, Raynaud's syndrome, and related disorders.

The venlafaxine dosage form of the invention improves efficacy and patient convenience by providing better tolerance to higher dosage strengths regarding adverse effects. The method provides a better safety profile in terms of gastrointestinal (nausea, constipation, anorexia, vomiting, flatulence), nervous system (somnolence, dry mouth, dizziness, insomnia, nervousness, abnormal dreams, tremor), special senses (blurred vision), urogenital (abnormal ejaculation, impotence), cardiovascular (sustained hypertension, hot flashes), body as a whole (asthenia), biochemical parameters and dermatological (sweating) systems. That is, the venlafaxine dosage form of the invention improves the side effect profile by reducing the frequency of occurrence or severity of the indicated side effects. In general, use of the osmotic device will provide a method of treating or preventing a disorder, disease or symptom responsive to venlafaxine therapy, wherein there is a lower incidence of adverse events compared to any other osmotic device. In some subjects, the osmotic device provides a decrease in the incidence of adverse events that generally appear at the initiation of therapy and during chronic therapy, wherein the adverse events would generally lead to discontinuation of treatment. In the open-label, randomized, parallel group study carried out as described in Example 3 the safety profile of the venlafaxine osmotic device of the invention showed reduced frequency of occurrence or severity of nausea, vomiting, and/or dizziness.

Generally venlafaxine can be administered at a starting dose of 37.5 mg/day for 4 to 7 days to allow new patients to adjust to the medication before increasing the dose in patient not responding to the starting dose. The dose increases are made in increments at intervals of not less than 4 days. The venlafaxine osmotic device of the invention can provide the patient an accelerated titration scheme for the initiation therapy, that is the intervals of the upward titration are shorter than the titration intervals permitted by venlafaxine dosage forms that release venlafaxine according to a different release profile. The venlafaxine osmotic device of the invention can provide the patient the possibility to receive a higher therapeutic dose at the initiation of the therapy and/or a higher maximum dose as needed, avoiding and/or decreasing the titration period.

It is known in the art that venlafaxine (VFX) has a pharmaceutically active metabolite O-desmethylvenlafaxine (ODV). The treatment schedule of the osmotic device of the invention improves the efficacy performance of venlafaxine by administering a patient a shorter treatment schedule that achieves therapeutic responses in a faster time than if the patient would have received another treatment schedule with a different dosage form containing the same amount of VFX. Thus, plasma-related efficacy concentrations is achieved more quickly for both, VFX and ODV. In this way, the osmotic device produces a faster onset of action compared to any other dosage form containing venlafaxine used for treating or preventing any disorder, disease or symptom that is responsive to venlafaxine therapy. The latency time for therapeutic activity is generally shortened by the use of this osmotic device.

The bioavailability study described in Example 2, conducted to investigate the pharmacokinetic behavior of three formulations of 150 mg strengths of venlafaxine osmotic tablets of Example 1 containing 10% (formulation T1), 20% (formulation T2) and 30% (formulation T3) of sodium chloride in the core respectively, compared to that of the reference product Effexor XR 150 mg (formulation R). Blood samples were withdrawn pre-dose and after 0.5, 1, 1.5, 2, 3, 4, 6, 8, 10, 12, 14, 16, 20, 24, 28, 36, 48, 72 hours post-dose. Plasma concentrations of venlafaxine and its active metabolite o-desmethylvenlafaxine were determined by an HPLC method with fluorescence detection (limit of quantitation of 1.0 ng/ml).

Table 1 contains the main pharmacokinetic parameters (mean±SD, n=14) observed for venlafaxine and its active metabolite that reflect the extent of absorption by AUC, the rate and extent of absorption by Cmax and the rate of absorption by Tmax.

TABLE 1

| Formulation | Tmax H | AUC ng*h/ml | Cmax ng/ml |
|---|---|---|---|
| Venlafaxine | | | |
| Effexor XR | 6.80 ± 1.01 | 1701.7 ± 1106.79 | 90.4 ± 38.20 |
| T1 | 11.20 ± 1.97 | 1846.4 ± 1145.63 | 70.5 ± 34.28 |
| T2 | 15.47 ± 4.03 | 1970.1 ± 1201.20 | 69.8 ± 33.85 |
| T3 | 17.07 ± 5.50 | 2124.7 ± 1418.90 | 71.3 ± 41.08 |
| O-Desmethylvenlafaxine | | | |
| Effexor XR | 10.13 ± 2.67 | 3664.4 ± 1400.73 | 131.0 ± 54.38 |
| T1 | 15.33 ± 3.98 | 3634.7 ± 1344.35 | 121.1 ± 50.04 |
| T2 | 18.67 ± 5.33 | 3574.1 ± 1322.04 | 107.9 ± 48.45 |
| T3 | 20.00 ± 5.86 | 3484.2 ± 1703.97 | 109.5 ± 58.17 |

Figure 3:
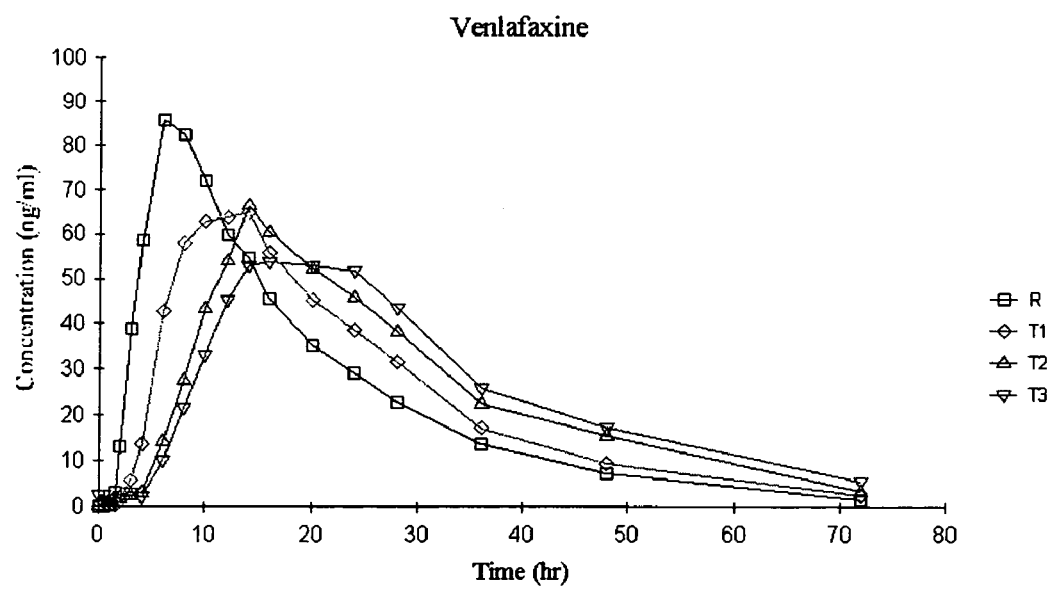
FIGS. 3 and 4 depict the mean concentration-time curves for venlafaxine and its metabolite in plasma respectively, provided by the administration of the formulations T1, T2, T3 and the reference Effexor XR (R).
Figure 4:
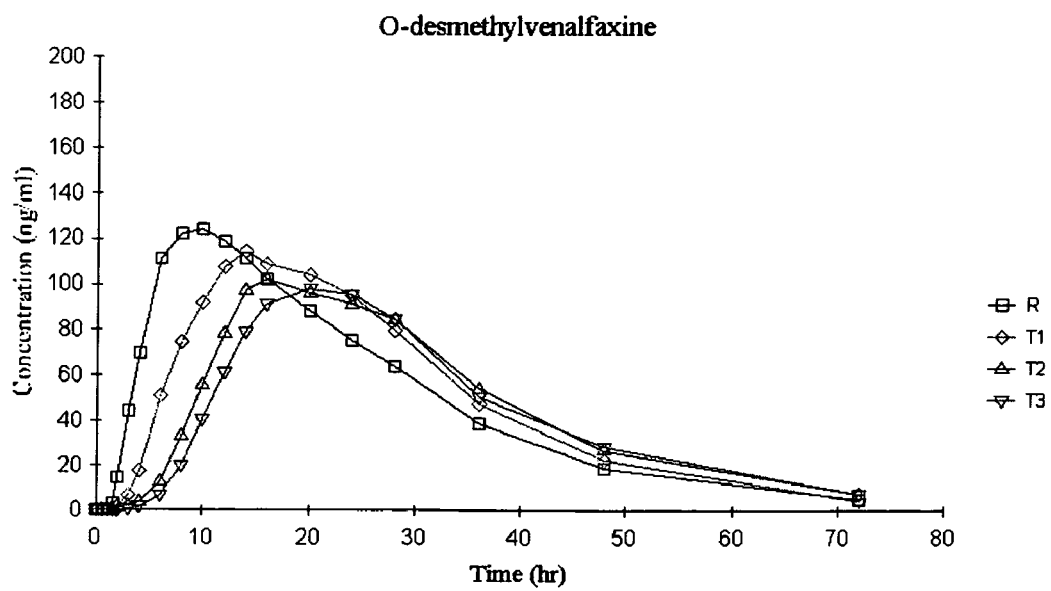

FIGS. 3 and 4 show the mean concentration-time curves found for venlafaxine and its metabolite in plasma respectively, provided by the administration of the test formulations T1, T2, T3 and the reference formulation Effexor ER (R).

Table 2 shows the test-to-reference ratios and 90% confidence intervals calculated from the log-transformed parameters after ANOVA for crossover designs.

TABLE 2

| Formulation | Venlafaxine | | O-desmethylvenlafaxine | |
|---|---|---|---|---|
| | AUC | Cmax | AUC | Cmax |
| T1 | 108.14 | 77.37 | 98.65 | 91.35 |
| | 89.06-131.32 | 69.55-86.08 | 85.16-114.27 | 80.50-103.65 |
| T2 | 110.77 | 74.79 | 96.29 | 81.17 |
| | 90.80-135.13 | 67.24-83.19 | 83.16-111.50 | 71.55-92.07 |
| T3 | 112.45 | 72.46 | 88.33 | 79.52 |
| | 92.26-137.05 | 65.14-80.59 | 76.32-102.24 | 70.10-90.20 |

The test-to-reference ratios showed a statistically significant reduction in Cmax for T1, T2 and T3 compared to the commercial reference product Effexor XR, without any statistically meaningful difference of the extent of absorption as measured by AUC. Additionally, a significantly increased Tmax for venlafaxine and its active metabolite was found. According to the Tmax values found in healthy subjects, these osmotic formulations were able to deliver the drug along the whole GI tract including the colon.

Figure 5:
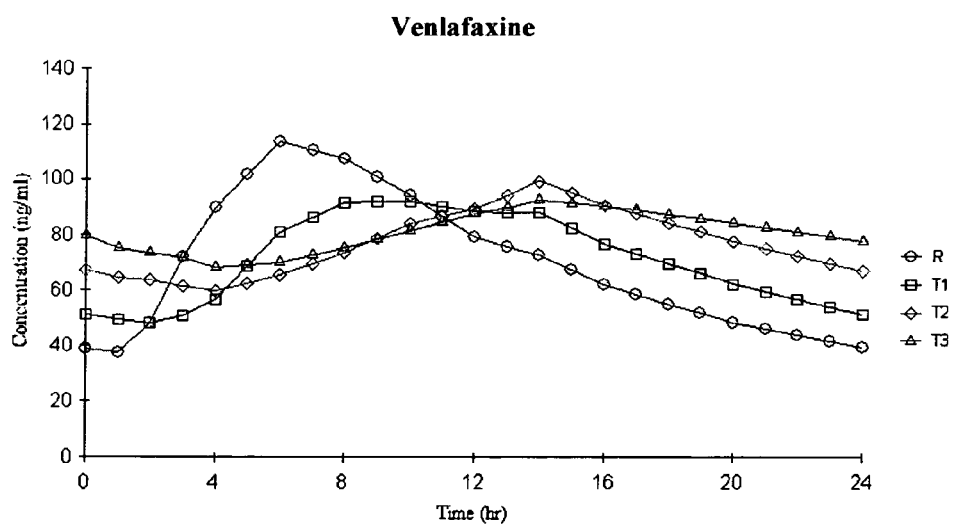
FIGS. 5 and 6 depict the peak-trough fluctuations of plasma concentrations of venlafaxine and its active metabolite respectively, obtained from a simulation in steady state by non-parametric superposition of single-dose curves using formulations T1, T2, T3 and Effexor XR (R).
Figure 6:
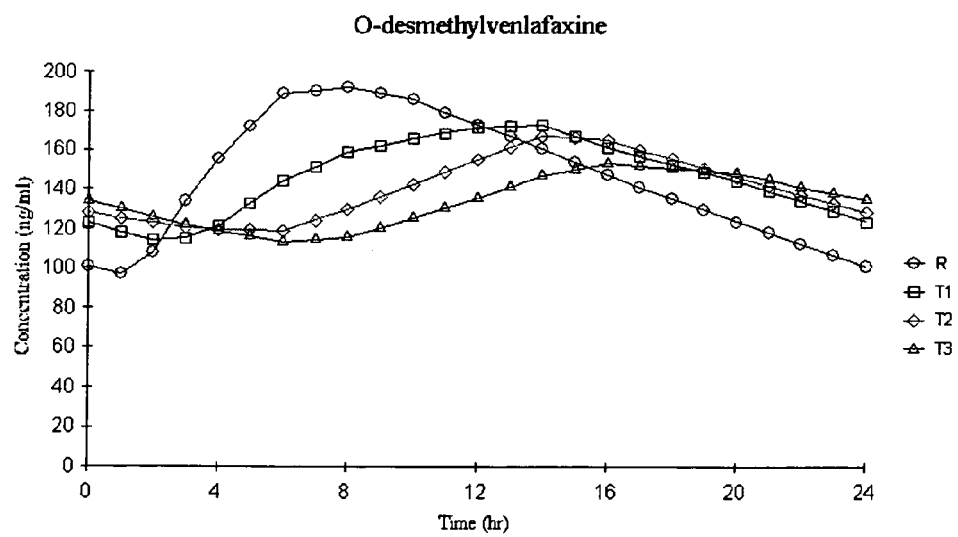

A simulation in steady state by non-parametric superposition of single-dose curves suggested that the therapeutic levels of venlafaxine and its active metabolite would be reached by the osmotic formulations T1, T2, and T3 with a great deal reduction, up to 3-fold, in peak-trough fluctuations of plasma concentrations, as showed in Table 3 and FIGS. 5 and 6.

TABLE 3

| Formulation | AUC ng*h/ml | Cmax ng/ml | Cmin ng/ml | Cav ng/ml | Fluctuation % |
|---|---|---|---|---|---|
| O-desmethylvenlafaxine | | | | | |
| Effexor XR | 3556.5 | 191.8 | 97.2 | 148.2 | 63.8 |
| T1 | 3516.9 | 172.2 | 114.2 | 146.5 | 39.6 |
| T2 | 3366.8 | 166.9 | 118.5 | 140.3 | 34.5 |
| T3 | 3209.7 | 152.9 | 113.1 | 133.7 | 29.7 |
| Venlafaxine | | | | | |
| Effexor XR | 1698.6 | 113.8 | 37.2 | 70.8 | 108.3 |
| T1 | 1716.9 | 91.9 | 48.1 | 71.5 | 61.2 |
| T2 | 1848.1 | 99.2 | 59.3 | 77.0 | 51.8 |
| T3 | 1933.2 | 92.1 | 67.9 | 80.6 | 30.1 |

Due to the VFX release profile provided by the osmotic device, it can provide less drug-drug interaction than another osmotic device comprising the same amount of VFX but releasing VFX according to a different profile. Thus, patients can be coadministered venlafaxine and another drug according to their therapeutic requirements while minimizing the extent of drug-drug interaction. Proof of this advantage is obtained by administering to a subject two different dosage form combinations at different time points: a first combination comprising a first dosage form and an osmotic device according to the invention; and a second combination comprising the first dosage form and another dosage form the releases VFX according to a release profile different than that provided by the present osmotic device. When the subject is administered the first combination, the subject will experience less drug-drug interactions than when s/he is administered the second combination.

The invention includes an osmotic device for the combined administration of venlafaxine and a second active drug in a controlled release manner from the core, e.g. an NMDA receptor antagonist selected from the group consisting of amantadine, memantine and ifenprodil. Co-administration of antidepressants, such as venlafaxine, with NMDA receptor antagonists, such as amantadine, may induce more pronounced antidepressive activity than treatment with antidepressants alone (Rogóz et al., (Eur. Neuropsychopharmacol. 11, Suppl. 2, S47, P.1.23, 2001).

The following examples should not be considered exhaustive, but merely illustrative of only a few of the many embodiments contemplated by the present invention. The methods described herein can be followed to prepare osmotic devices according to the invention.

Example 1

Venlafaxine HCl osmotic device tablets of 75 and 150 mg strengths comprising coating A, and 0, 20 and 52% of sodium chloride in the core, and venlafaxine HCl osmotic device tablets of 75 and 150 mg strengths comprising coating B and 0, 5, 10, 15, and 30% of sodium chloride in the core were manufacture with the following general method. Venlafaxine hydrochloride (42.43 mg and 169.7 mg), a diluent (0-150 mg), and a binder (10-18 mg), were first individually screened to a uniform size using a Quadro Comil at less than 1,000 rpm, and then mixed with sodium chloride previously milled using a Fitz Mill with a screen 0020-0069 at less than 8000 rpm, in a mixer granulator for up to 25 minutes to form a homogenous powder blend. The granulation process was initiated by adding a solution containing a plasticizer of low molecular weight (2-15 mg) and a plasticizer of higher molecular weight (0-85 mg) in purified water for granules. The wet granulation was sieved through a Quadro Comil at a speed less than 1000 rpm, and then dried in a static bed at 50° C. for humidity reduction. Next, the dry granules are milled using a Quadro Comil with a screen R991μ at less than 2,000 rpm for size reduction. Then, a mixture of a glidant (0.2-5 mg) and a lubricant (1-7 mg), previously sieved through a 100 mesh screen, was added and mixed for about 15 minutes. The resulting mixture was compressed in a compressor with 8.0 mm diameter punches to form uncoated cores. The average weight of the 75 mg strength uncoated cores was approximately between 210 to 300 mg. The average weight of the 150 mg strength uncoated cores was approximately between 310 to 300 mg.

The 75 mg strength uncoated cores were then coated with coating A prepare as follows: a solution containing cellulose ester 1 (11-18.5 mg), cellulose ester 2 (6.5-12 mg), and plasticizer of low molecular weight (1-3 mg) in a blend of methylene chloride and methanol, to form semipermeable membrane coated cores. The membrane coating weighed approximately between 24 and 28.14 mg.

The 150 mg strength uncoated cores were then coated with coating B prepare as follows: a solution containing cellulose ester 1 (4.5-8 mg), cellulose ester 2 (15-20 mg), and a plasticizer of low molecular weight (1-3 mg) in a blend of acetone and purified water, to form semipermeable membrane coated cores. The membrane coating weighed approximately between 21.50 and 27.9 mg.

The semipermeable membrane coat of each core was then perforated with laser equipment to form at least one passageway of 0.2-0.8 mm through the semipermeable coat.

In one embodiment, the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide); the cellulose ester is selected from the group consisting of cellulose acetate, cellulose acylate, cellulose fatty acid ester, and cellulose acetate phthalate; the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate; the lubricant is selected from the group consisting of calcium stearate, magnesium stearate, mineral oil, stearic acid, and zinc stearate; the diluent is selected from the group consisting of microcrystalline cellulose, lactose, sucrose, mannitol, cellulose, starch, sorbitol, dibasic calcium phosphate, and calcium carbonate; and the glidant is selected from the group consisting of colloidal silica, cornstarch, talc, calcium silicate, magnesium silicate, colloidal silicon, and silicon hydrogel.

Example 2

The following general method is used to administer three different venlafaxine-containing osmotic devices of Example 1 to human patients and to evaluate its in vivo performance. The bioavailability of the osmotic device is evaluated using a single-dose, cross-over randomized pharmacokinetic study with a one-week washout period. Three formulations of (150 mg strength of venlafaxine) osmotic tablets according to Example 1 and containing 10% (formulation T1), 20% (formulation T2) and 30% (formulation T3) of sodium chloride in the core respectively are compared to EFFEXOR XR. Healthy hospitalized subjects (non-smokers between the ages of 21-50) were randomly separated into equally sized groups. Each group receive the above mentioned formulations, one per period. Blood samples are taken periodically from 0 to 48 hrs after administration and plasma aliquots are obtained immediately and stored at −20° C. for later analysis by HPLC to determine VFX and ODV content. The following pharmacokinetic parameters are calculated from the plasma concentration curves for each formulation and each subject: area under the curve from 0-48 hrs ($AUC_{0-t}$) and extrapolated to infinity ($AUC_{0-inf}$); maximum concentration of VFX and ODV in plasma ($C_{max}$); and time to reach $C_{max}$ ($T_{max}$). Statistical comparisons are made using Analysis of Variance (ANOVA) for the crossover design. Safety is evaluated by physical examination, vital signs, laboratory examinations, electrocardiogram, ambulatory blood pressure measurement, and adverse event records. Specifically, the incidence of gastrointestinal, nervous system, urogenital, cardiovascular and dermatological adverse events is calculated.

A lower Cmax or a longer Tmax for either VFX or ODV, or a lower incidence of adverse events between the venlafaxine osmotic device of the Example 1 and EFFEXOR XR is indicative of the improvement in the formulation.

Example 3

An open-label, randomized, parallel group study is carried out in adult patients to compare the safety profile of the venlafaxine osmotic device of the invention vs Effexor XR.

Patients with a diagnosis of Major Depression Disorder based on DSM IV are administered 150 mg strength of the venlafaxine osmotic device of the invention and 150 mg strength of Effexor XR during four weeks, for both dosages.

Safety evaluations are done on a weekly basis, specially regarding the appearance of nausea, constipation, anorexia, vomits, somnolence, dry mouth, dizziness, insomnia, nervousness, tremor, blurred vision, abnormal ejaculation, impotence, sexual dysfunction, sustained hypertension, hot flashes, asthenia, and/or sweating. Standardized scales are used for measurement of each parameter.

Visual Analogue Scale 0-100 mm and Likert 5-point category-scales are used for nausea, anorexia, dizziness, dry mouth and sweating. The Rush Sexual Inventory (YES-NO questionnaire with five Visual Analogue Scales) is used for sexual disorders. Athens Scale is employed for insomnia and Epworth Sleepiness Scale for somnolence.

Less incidence of any of the above mentioned adverse events, discontinuation and/or drop-outs due to safety issues is indicative of an improvement in the safety profile of the osmotic device.

Example 4

The following procedure is used to prepare osmotic device formulations containing venlafaxine (150 and 200 mg strength) and amantadine (100 mg strength) in separate stacked layers in the core of the osmotic device. The osmotic device formulations contain the following ingredients in the amounts indicated:

| Ingredients | Amount (mg) | |
| --- | --- | --- |
| Venlafaxine strength | 150 | 250 |
| Amantadine strength | 100 | 100 |
| Core | | |
| Venlafaxine HCl | 169.72 | 282.87 |
| Amantadine HCl | 100.00 | 100.00 |
| Mannitol | 32.28 | 46.13 |
| Microcrystalline Cellulose PH 101 | 70.00 | 92.00 |
| Povidone K-90 | 12.00 | 17.00 |
| Microcrystalline Cellulose PH 200 | 10.00 | 13.00 |
| Colloidal Silicon Dioxide | 2.00 | 3.00 |
| Magnesium Stearate | 4.00 | 6.00 |
| Purified Water | 60.00 | 84.00 |
| Coating A | | |
| Cellulose Ester | 23.75 | 28.50 |
| Polyethylene Glycol 400 | 1.25 | 1.50 |
| Acetone | 500.00 | 600.00 |
| Coating B | | |
| Opadry Y 1 18128 A White | 13.00 | 18.00 |
| Purified Water | 130.00 | 180.00 |

Venlafaxine hydrochloride, amantadine hydrochloride, mannitol, microcrystalline cellulose PH 101, and povidone K-90 were first individually screened to a uniform size using a Quadro Comil at less than 500 rpm, in a mixer granulator for up to 5 minutes to form a homogeneous powder blend.

The granulation process was initiated by the gradual addition of purified water to the powder blend, with continuous mixing, to change the consistency of the dry powder ingredients to granules. The wet granulation was sieved through a Quadro Comil at a speed less than 500 rpm, and then dried in a static bed at 500 C for humidity reduction. Next, the dry granules were milled using a Quadro Comil with a screen R991μ at less than 1000 rpm for size reduction.

Then, a mixture of magnesium stearate and colloidal silicone dioxide, previously sieved through a 40 mesh screen, was added and mixed for about 5 minutes. The resulting mixture was compressed in a compressor with 10.5-12 mm diameter punches to form uncoated cores. The average weight of the uncoated cores was approximately between 450 to 650 mg.

An osmotic coating composition was prepared as follows: cellulose ester and polyethylene glycol were blended in acetone and purified water. The blend was sprayed onto the uncoated cores to obtain coated cores. The membrane coating of each core was then perforated with laser equipment to form at least one passageway of 0.2-0.8 mm through the semipermeable coat.

A final coating composition was prepared as follows: Opadry was blended in water. The blend was sprayed onto the uncoated cores to obtain coated cores.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. An osmotic device comprising:
   a unitary core comprising venlafaxine salt, one or more excipients and osmotic salt wherein the weight ratio of venlafaxine salt to osmotic salt ranges from 0.35:1 to 150:1; and
   a semipermeable membrane surrounding the core and having one or more passageways there through;
   wherein the drug salt is released through the one or more passageways according to a sigmoidal controlled release profile when the osmotic device is exposed to an aqueous environment of use, wherein the drug salt and osmotic salt have a common ion, and wherein release of venlafaxine salt is delayed for a period of 30 min to 10 hours, said delay being caused by the osmotic salt in the core.

2. The osmotic device of claim 1, wherein the venlafaxine salt is a venlafaxine mineral acid salt, and the osmotic salt is an alkali metal salt.

3. The osmotic device of claim 2, wherein the alkali metal salt is sodium chloride and the mineral acid is hydrogen chloride.

4. The osmotic device of claim 1, wherein the venlafaxine salt is a venlafaxine organic acid salt, and the osmotic salt is an organic salt.

5. The osmotic device of claim 1, wherein the venlafaxine salt is venlafaxine succinate and the osmotic salt is sodium succinate or magnesium succinate.

6. The osmotic device of claim 1, wherein the venlafaxine salt is venlafaxine fumarate and the osmotic salt is sodium fumarate.

7. The osmotic device of claim 1, wherein the venlafaxine salt is venlafaxine citrate and the osmotic salt is sodium citrate.

8. The osmotic device of claim 1, wherein the venlafaxine salt is venlafaxine butyrate and the osmotic salt is sodium butyrate.

9. An osmotic device comprising:
a) a unitary core comprising a mixture of venlafaxine hydrochloride, one or more excipients and sodium chloride, wherein crystals of the sodium chloride are not coated with cellulose acetate butyrate, wherein the weight ratio of venlafaxine hydrochloride to sodium chloride is 0.35:1 to 150:1; and
b) a semipermeable membrane surrounding the core and having one or more passageways there through;
wherein the drug salt is released through the one or more passageways according to a sigmoidal controlled release profile when the osmotic device is exposed to an aqueous environment of use, wherein the drug is not pseudoephedrine or oxybutynin, and wherein release of venlafaxine hydrochloride is delayed for a period of 30 min to 10 hours, said delay being caused by the sodium chloride in the core.

10. An osmotic device comprising:
a) a unitary core comprising venlafaxine hydrochloride, one or more excipients, and sodium chloride, wherein the weight ratio of venlafaxine hydrochloride to sodium chloride is 0.35:1 to 150:1; and
b) a semipermeable membrane surrounding the core and having one or more passageways there through, the membrane having a controlled porosity or permeability adapted to cooperate with the sodium chloride to provide a predetermined release profile for venlafaxine hydrochloride;
wherein the sodium chloride is present in an amount sufficient such that venlafaxine hydrochloride is released through the one or more passageways according to a sigmoidal controlled release profile when the osmotic device is exposed to an aqueous environment of use, and wherein release of venlafaxine hydrochloride is delayed for a period of 30 min to 10 hours, said delay being caused by sodium chloride in the core.

11. The osmotic device of claim 10, further comprising a second active drug in the core.

12. The osmotic device of claim 11, wherein the second active drug is amantadine.

13. The osmotic device of claim 1, wherein the venlafaxine salt is present at 37.5 mg, 75 mg or 150 mg strength.

14. The osmotic device of claim 1, wherein the osmotic salt is present at 10%, 15%, 20%, 30%, or 52% wt. of the core.

15. The osmotic device of claim 1, wherein the semipermeable membrane comprises cellulose ester and a plasticizer.

16. The osmotic device of claim 15, wherein the cellulose ester is selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates.

17. The osmotic device of claim 15, wherein the plasticizer is selected from low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly (ethylene glycol), citrate ester-type plasticizers, triacetin, propylene glycol and glycerin.

18. The osmotic device of claim 15, wherein the cellulose ester is cellulose acetate (CA) and the plasticizer is poly (ethylene glycol).

19. The osmotic device of claim 18, wherein the ratio of cellulose acetate to poly(ethylene glycol) ranges from 50-99% by weight of CA:50-1% by weight of PEG, and about 95% by weight of CA:about 5% by weight of PEG.

20. The osmotic device of claim 1 comprising:
a unitary core comprising: venlafaxine hydrochloride present at 37.5 mg, 75 mg or 150 mg strength; sodium chloride present at 10% to 52% wt. of the core; binder present at 10-18 mg; and plasticizer present at 2-100 mg;
a membrane surrounding the core, having at least one passageway of 0.2-0.8 mm there through, and comprising two cellulose esters and a plasticizer.

21. The osmotic device of claim 20 comprising:
a unitary core comprising: venlafaxine hydrochloride present at 37.5 mg, 75 mg or 150 mg strength; sodium chloride present at 10% to 52% wt. of the core; diluent; binder present at 10-18 mg; low molecular weight plasticizer present at 2-15 mg; and higher molecular weight plasticizer present at 0-85 mg;
a membrane surrounding the core, having at least one passageway of 0.2-0.8 mm there through, and comprising two cellulose esters and a plasticizer.

22. The osmotic device of claim 21 comprising:
a unitary core comprising: venlafaxine hydrochloride present at 37.5 mg, 75 mg or 150 mg strength; sodium chloride present at 10% to 52% wt, of the core; diluent; binder present at 10-18 mg; low molecular weight plasticizer present at 2-15 mg; and higher molecular weight plasticizer present at 0-85 mg;
a membrane surrounding the core, having at least one passageway of 0.2-0.8 mm there through, and comprising two cellulose esters and a plasticizer, wherein: a) the first cellulose ester is present at 11-18.5 mg, the second cellulose ester is present at 6.5-12 mg, and the plasticizer is present at 1-3 mg, and the membrane weighs 24-28.14 mg; or b) the first cellulose ester is present at 4.5-8 mg, the second cellulose ester is present at 15-20 mg, and the plasticizer is present at 1-3 mg, and the membrane weighs 21.5 to 27.9 mg.

23. The osmotic device of claim 22 comprising:
a unitary core comprising: venlafaxine hydrochloride present at 37.5 mg, 75 mg or 150 mg strength; sodium chloride present at 10% to 52% wt. of the core; diluent present at 0-150 mg; binder present at 10-18 mg; low molecular weight plasticizer present at 2-15 mg; higher molecular weight plasticizer present at 0-85 mg; glidant present at 0.2-5 mg; and lubricant present at 1-7 mg;
a membrane surrounding the core, having at least one passageway of 0.2-0.8 mm there through, and comprising two cellulose esters and a plasticizer, wherein: a) the first cellulose ester is present at 11-18.5 mg, the second cellulose ester is present at 6.5-12 mg, and the plasticizer is present at 1-3 mg, and the membrane weighs 24-28.14 mg; or b) the first cellulose ester is present at 4.5-8 mg, the second cellulose ester is present at 15-20 mg, and the plasticizer is present at 1-3 mg, and the membrane weighs 21.5 to 27.9 mg.

24. The osmotic device of claim 23, wherein:
the binder is selected from the group consisting of poly (vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);

the cellulose ester is selected from the group consisting of cellulose acetate, cellulose acylate, cellulose fatty acid ester, and cellulose acetate phthalate;

the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate;

the lubricant is selected from the group consisting of calcium stearate, magnesium stearate, mineral oil, stearic acid, and zinc stearate;

the diluent is selected from the group consisting of microcrystalline cellulose, lactose, sucrose, mannitol, cellulose, starch, sorbitol, dibasic calcium phosphate, and calcium carbonate; and the glidant is selected from the group consisting of colloidal silica, cornstarch, talc, calcium silicate, magnesium silicate, colloidal silicon, and silicon hydrogel.

25. A method of treating or preventing a disorder, disease or symptom responsive to venlafaxine therapy, the method comprising the step of administering to a subject an osmotic device according to any one of claims 1, 9, 10, 20-22 or 23, wherein one or more of the side effects observed in the subject are of lesser occunence or severity than the side effects observed in the same subject administered another dosage form comprising substantially the same amount of venlafaxine hydrochloride but releasing the venlafaxine hydrochloride according to a different release profile.

26. The method of claim 25, wherein the side effects are nausea, constipation, anorexia, vomits, flatulence, somnolence, dry mouth, dizziness, insomnia, nervousness, abnormal dreams, tremor, bluned vision, abnormal ejaculation, impotence, sexual dysfuntion, sustained hypertension, hot flashes, asthenia, and/or sweating.

27. A method of treating or preventing a disorder, disease or symptom responsive to venlafaxine therapy, the method comprising the step of administering to a subject an osmotic device according to claims 1, 9, 10, 20-22 or 23, wherein the intervals of the upward titration observed in the subject are shorter than the intervals of the upward titration observed in the same subject administered another dosage form comprising substantially the same amount of venlafaxine hydrochloride but releasing the venlafaxine hydrochloride according to a different release profile.

28. A method of treating or preventing a disorder, disease or symptom responsive to venlafaxine therapy, the method comprising the step of administering to a subject an osmotic device according to claim 1, 9, 10, 20-22 or 23, wherein the peak-trough fluctuations of plasma concentrations observed in the subject is lower than the peak-trough fluctuations of plasma concentrations observed in the same subject administered another dosage form comprising substantially the same amount of venlafaxine but releasing the venlafaxine according to a different release profile.

29. A method of reducing drug-drug interactions in a subject comprising the step of administering to the subject a first dosage form comprising a first drug and an osmotic device according to claim 1, 9, 10, 20-22 or 23 instead of administering to the subject the first dosage form comprising the first drug and another dosage form comprising substantially the same amount of venlafaxine but releasing the venlafaxine according to a different release profile, thereby obtaining in the subject a venlafaxine release profile that is less conducive to producing drug-drug interactions between the first drug and venlafaxine 30. A method for providing in a subject a therapeutic plasma concentration of VFX over a 24-hour period with reduced nausea and emesis, the method comprising administering to the subject an osmotic device according to claim 1, 9, 10, 20-22 or 23 that provides a peak plasma level of venlafaxine during the period of from about 9 to about 28 hours after administration.

* * * * *